US008197525B2

(12) United States Patent
Pierre et al.

(10) Patent No.: US 8,197,525 B2
(45) Date of Patent: Jun. 12, 2012

(54) FULL BODY SPLIT ACCESS BLANKET

(75) Inventors: Joseph Pierre, Brockton, MA (US);
Rachel Starr, Randolph, MA (US);
Alan Stec, East Bridgewater, MA (US)

(73) Assignee: Smiths Medical ASD, Inc., Rockland, MA (US)

( * ) Notice: Subject to any disclaimer, the term of this patent is extended or adjusted under 35 U.S.C. 154(b) by 462 days.

(21) Appl. No.: 12/379,160

(22) Filed: Feb. 13, 2009
(Under 37 CFR 1.47)

(65) Prior Publication Data
US 2010/0211138 A1    Aug. 19, 2010

(51) Int. Cl.
*A61F 7/00*    (2006.01)
(52) U.S. Cl. ......................................... 607/104
(58) Field of Classification Search .............. 607/104, 607/96
See application file for complete search history.

(56) References Cited

U.S. PATENT DOCUMENTS

| | | | |
|---|---|---|---|
| 5,097,548 A * | 3/1992 | Heck et al. ............... | 5/482 |
| 5,735,890 A | 4/1998 | Kappel et al. | |
| 5,773,275 A | 6/1998 | Anderson et al. | |
| 5,839,133 A | 11/1998 | Dickerhoff et al. | |
| 6,036,722 A * | 3/2000 | Augustine ................ | 607/104 |
| 6,113,626 A * | 9/2000 | Clifton et al. .......... | 607/96 |
| 6,290,716 B1 * | 9/2001 | Augustine ................ | 607/104 |
| 6,440,157 B1 * | 8/2002 | Shigezawa et al. ....... | 607/96 |
| 6,511,501 B1 | 1/2003 | Augustine et al. | |
| 6,519,964 B2 * | 2/2003 | Bieberich .............. | 62/259.3 |
| 7,066,949 B2 * | 6/2006 | Gammons et al. ......... | 607/107 |
| 7,244,268 B2 * | 7/2007 | Arnold et al. ............ | 607/104 |
| 7,520,889 B2 * | 4/2009 | Van Duren .............. | 607/104 |
| 7,550,000 B2 * | 6/2009 | Frey .................... | 607/104 |
| 7,871,428 B2 * | 1/2011 | Augustine .............. | 607/107 |
| 7,871,429 B2 * | 1/2011 | Anderson et al. ........ | 607/107 |
| 7,931,682 B2 * | 4/2011 | Albrecht et al. ........ | 607/108 |
| 7,951,184 B2 * | 5/2011 | Schuessler et al. ...... | 607/107 |
| 2002/0107558 A1 * | 8/2002 | Clifton et al. .......... | 607/104 |
| 2008/0082150 A1 * | 4/2008 | Schock et al. ........... | 607/96 |
| 2010/0198320 A1 * | 8/2010 | Pierre et al. ............ | 607/107 |

OTHER PUBLICATIONS

PCT International Search Report and Written Opinion, ISA/KR, Oct. 7, 2010.

* cited by examiner

*Primary Examiner* — Christopher D Koharski
*Assistant Examiner* — Diva K Chander
(74) *Attorney, Agent, or Firm* — Louis Woo

(57) ABSTRACT

A full body blanket has a central bonded strip that extends from a distal end of an upper portion of the blanket to the foot end of the blanket to divide the main body of the blanket into two longitudinal portions. A discontinuous slit or tearable line is provided along the length of the strip to enable the longitudinal portions to be separable from each other by a user applying a force along the tearable strip. The strip may be torn anywhere along its entire length so that the longitudinal portion to be removed from the patient may be folded back anywhere along the length of the strip to selectively expose particular body parts of the patient. The blanket is inflated by heated air, and the heated air is circulated by channels that extend longitudinally along each of the longitudinal portions. Rows of apertures provided along the channels at the layer of the blanket that makes contact with the patient output the heated air to warm the patient.

20 Claims, 4 Drawing Sheets

FULL BODY SPLIT ACCESS BLANKET

FIELD OF THE INVENTION

The present invention relates to convective warming blankets and more particularly relates to a full body blanket having portions thereof that are removable relative to the rest of the blanket so that a clinician or surgeon can gain access to a particular area of the body of the patient covered by the blanket.

BACKGROUND OF THE INVENTION

Full body convective warming blankets are known. Such full body blankets cover the body of the patient for maintaining the temperature of the patient before, during and after a surgical operation, or to maintain the body temperature of the patient to prevent the patient from going into hypothermic shock. During a surgical operation, prior to the present invention, to cover those areas of the body of the patient that are not being operated on, a number of half body blankets are used. The use of multiple blankets during a surgical operation is cumbersome, not to mention that multiple warmers are needed to inflate the multiple blankets.

SUMMARY OF THE PRESENT INVENTION

The convective warming blanket of the present invention is a full body blanket that covers the body of the patient and allows the clinician or surgeon to gain access to different body areas the patient. The blanket has an upper portion and two longitudinal portions removably connected to each other that extend from the upper portion. The longitudinal portions form a substantial part of the blanket, and are connected to each other by a bonded strip—with a discontinuous slit, weakened portion or tearable line extending along the strip—that allows the longitudinal portions to be separated from each other. Once separated, the of interest longitudinal portion is removed relative to the rest of the blanket to selectively expose a particular body area of the patient. The longitudinal portions may be considered the splitable parts of the blanket. The blanket of the present invention is therefore a full body split access blanket.

In particular, the blanket of the present invention is made of two air impermeable sheets that are bonded at their respective edges to form an inflatable structure. The dimension of the blanket is such that it is a full body blanket that has an upper portion and two longitudinal portions that extend from the distal end of the upper portion, with a bonded strip that may be considered to be a continuation of the edges of the blanket formed between and connecting the two longitudinal portions. A discontinuous slit, a weakened line or a tearable area, etc., is provided along the length of the strip from the distal end of the upper portion of the blanket to the foot end of the blanket. When a given force is applied to separate the strip along the discontinuous slit, as for example by starting a tear along the strip at the foot end of the blanket, the longitudinal portions are detachable from each other, so that the detached longitudinal portion is removable from the rest of the blanket anywhere along the longitudinal strip to expose selective body parts of the patient, i.e., allow access to the selective body parts of the patient.

The blanket of the present invention is a full body blanket that covers the patient from his shoulders to his feet. A cut out is provided at the head end of the blanket to enable the head of the patient to be exposed while the patient's body is covered by the blanket.

Two inlet ports are provided in the blanket, preferably at or near the shoulder covering portions of the blanket, to allow temperature treated air, for example heated air to be pumped into the blanket to thereby inflate the same. On the sheet that comes into contact with the patient, a plurality of apertures are provided to allow the temperature treated air to output from the blanket to warm the body of the patient. At the distal area at each of the splitable longitudinal portions of the blanket there is a sealed portion that covers the foot of the blanket.

To circulate the heated air, a plurality of longitudinal channels are provided along each of the splitable longitudinal portions. Each of the channels is formed by adjacent spaced apart seals that bondedly attach the two air impermeable sheets. The plurality of apertures formed on the sheet of the blanket that comes into contact with the patient is formed as longitudinal rows of apertures. Except for the two outermost longitudinal peripheral edge seals that bond the upper and lower sheets of the blanket, each of the interior longitudinal seals that together form the air circulation longitudinal channels of the blanket has a row of apertures formed adjacent thereto.

The present invention therefore is directed to a convective warming blanket that comprises two air impermeable sheets bonded at their respective edges to form an inflatable structure that covers the body of a patient, the structure having an upper portion that covers at least the shoulder and an area proximate to the collar bone of the patient and a main body portion that includes at least two longitudinal portions each extending from a distal end of the upper portion to the foot end of the blanket. The longitudinal portions are removably attached to each other along a common bonded strip having a discontinuous slit or tearable line therealong so that the longitudinal portions are separable from each other along the strip. When one of the longitudinal portions is separated from the other of the longitudinal portions, it is moved away from the body of the patient independently from the rest of the blanket structure to expose an area of the body of the patient that previously had been covered by the removed longitudinal portion.

The present invention is also directed to a convective warming blanket for covering the body of the patient that comprises an inflatable structure having an upper portion, at least two longitudinal portions extending from a distal end of the upper portion to a foot end of the structure, the longitudinal portions removably connected by a bonded strip separable at different lengths therealong so that either one or other of the two longitudinal portions is movable relative to the rest of the structure away from the patient to allow access to selective parts of the body of the patient covered by the structure, the structure having at least one inlet to enable temperature treated air to be input to the structure.

The blanket of the present invention is moreover directed to a full body convective warming blanket that allows access to selective areas of the body of the patient covered thereby that is formed from two air impermeable sheets sealed at their respective edges, the blanket comprising an upper portion, at least one and other longitudinal portions removably connected to each other at a bonded strip extending longitudinally from a distal end of the upper portion to a foot end of the blanket, the bonded strip being tearable when a tearing force is applied thereto such that any section of the one and other longitudinal portions is separatable from each other along the length of the strip to enable one or other of the longitudinal portions to be removed from the body of the patient so as to expose selective parts of the body of the patient. The full body convective warming blanket further includes at least one inlet to allow heated air to be input to inflate the blanket, a plurality of channels formed longitudinally along each of the one and other longitudinal portions for guiding the flow of heated air along the blanket, and multiple rows of aperture formed at the sheet in contact with the patient for outputting the heated air to the patient.

BRIEF DESCRIPTION OF THE FIGURES

The present invention will become more apparent and the invention itself will be best understood by reference to the following description of the invention taken in conjunction with the following drawings, wherein.

DETAILED DESCRIPTION OF THE INVENTION

Figure 1:
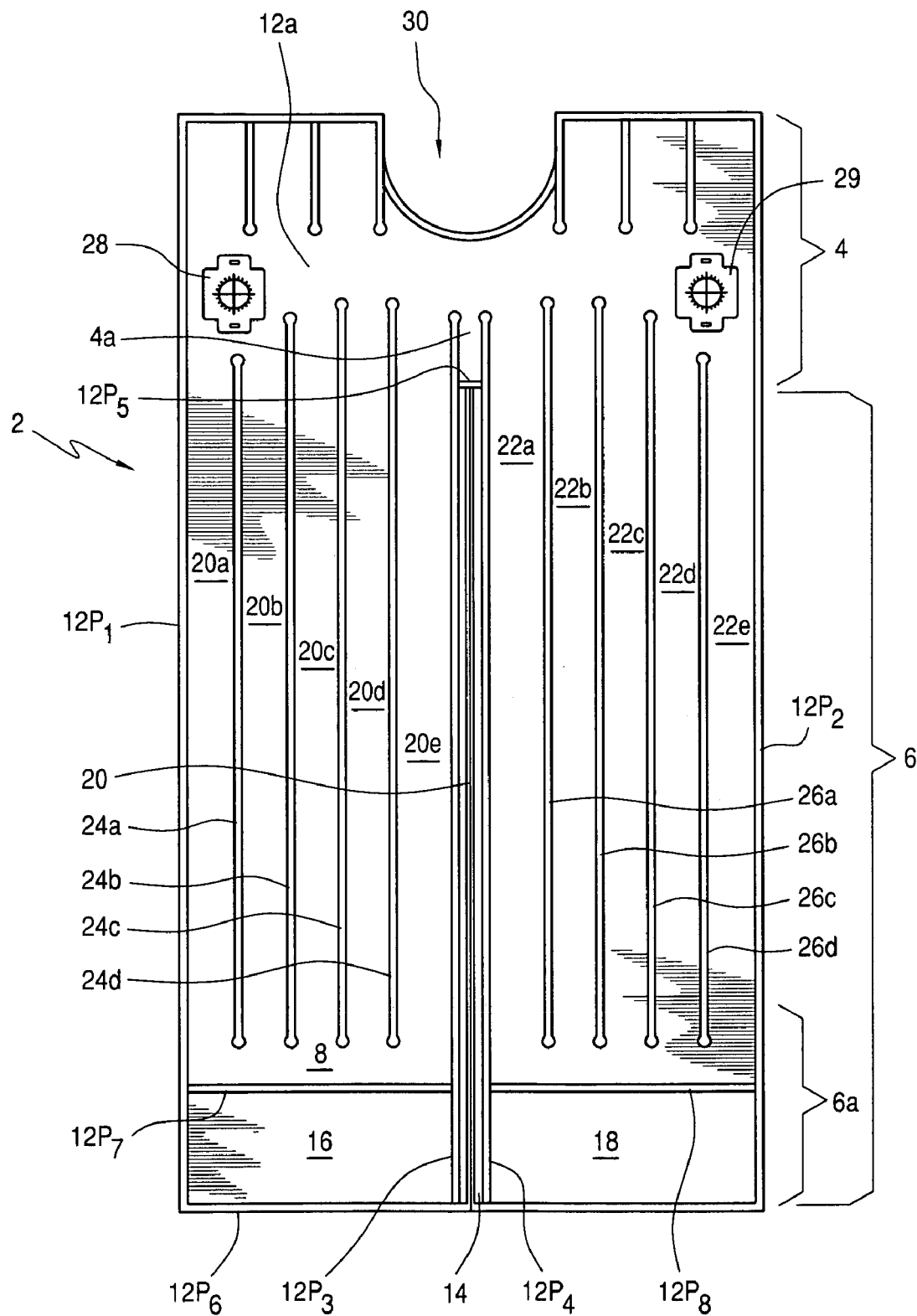
FIG. 1 is a plan view of the full body split access convective warming blanket of the present invention.

With reference to FIG. 1, the convective warming blanket of the present invention is shown to be a full body split access blanket 2 that has an upper portion 4 and a main body portion 6 that includes two splitable longitudinal portions 8 and 10. Blanket 2 is made of two air impermeable sheets, designated 12a for the upper or top sheet shown in FIG. 1 and 12b for the lower or bottom sheet shown in FIG. 2. As is well known, the two air impermeable sheets 12a and 12b are bonded at their respective edges or peripheries to form an air inflatable structure. The longitudinal peripheries of blanket 2 are shown by designations $12p_1$ and $12p_2$.

To form longitudinal portions 8 and 10, there are seals $12p_3$ and $12p_4$ that extend longitudinally parallel to seals $12p_1$ and $12p_2$ so as to form a bonded strip 14 that connects longitudinal portions 8 and 10. For ease of reference, the distal end 4a of upper portion 4 references the upper horizontal seal $12p_5$ that forms the upper end of strip 14. The foot end of the blanket 2 may be referenced by the lowermost seal $12p_6$. There are in addition horizontal seals $12p_7$ and $12p_8$ that together with the other mentioned seals form respective seal foot portions 16 and 18 for longitudinal portions 8 and 10, respectively.

Strip 14 has formed along its length, between edges $12p_5$ and $12p_6$, a discontinuous slit 20 that enables longitudinal portions 8 and 10 to be separable from each other. Instead of a discontinuous slit, 20 may be a weakened area or a tearable line along strip 14, preferably centered, that allows a user to apply a force, say for example by holding either of foot portions 16 and 18 and tearing or splitting either of longitudinal portions 8 and 10 from the other, i.e., moving the one longitudinal portion away from the rest of the blanket structure. Given that the tearable slit or line 20 extends from foot end $12p_6$ to the distal end of the upper portion 4, i.e., edge $12p_5$, the being removed longitudinal portion may be torn relative to the other longitudinal portion at any length or anywhere along strip 14.

At each of the longitudinal portions 8 and 10 there is provided a plurality of channels 20a-20e and 22a-22e, respectively. Each of the channels, except for the outermost channel 20a for longitudinal portion 8 and the outermost channel 22e for longitudinal portion 10, is formed by spaced apart seals that run longitudinally along the longitudinal portions 8 and 10. For longitudinal portion 8, the seals are outside peripheral seal $12p_1$, interior or inside seals 24a, 24b, 24c, 24d and strip periphery seal $12p_3$. For longitudinal portion 10, the seals are strip periphery seal $12p_4$, interior or inside seals 26a, 26b, 26c, 26d and outside periphery seal $12p_2$.

At the upper portion of blanket 2 there are two inlet ports 28 and 29 with respective openings that enable an air hose, not shown, to be mated thereto so that temperature heated fluid, for example heated air, may be pumped into blanket 2 to inflate the same. Under normal operation, only one of the inlet ports is used.

Figure 2:
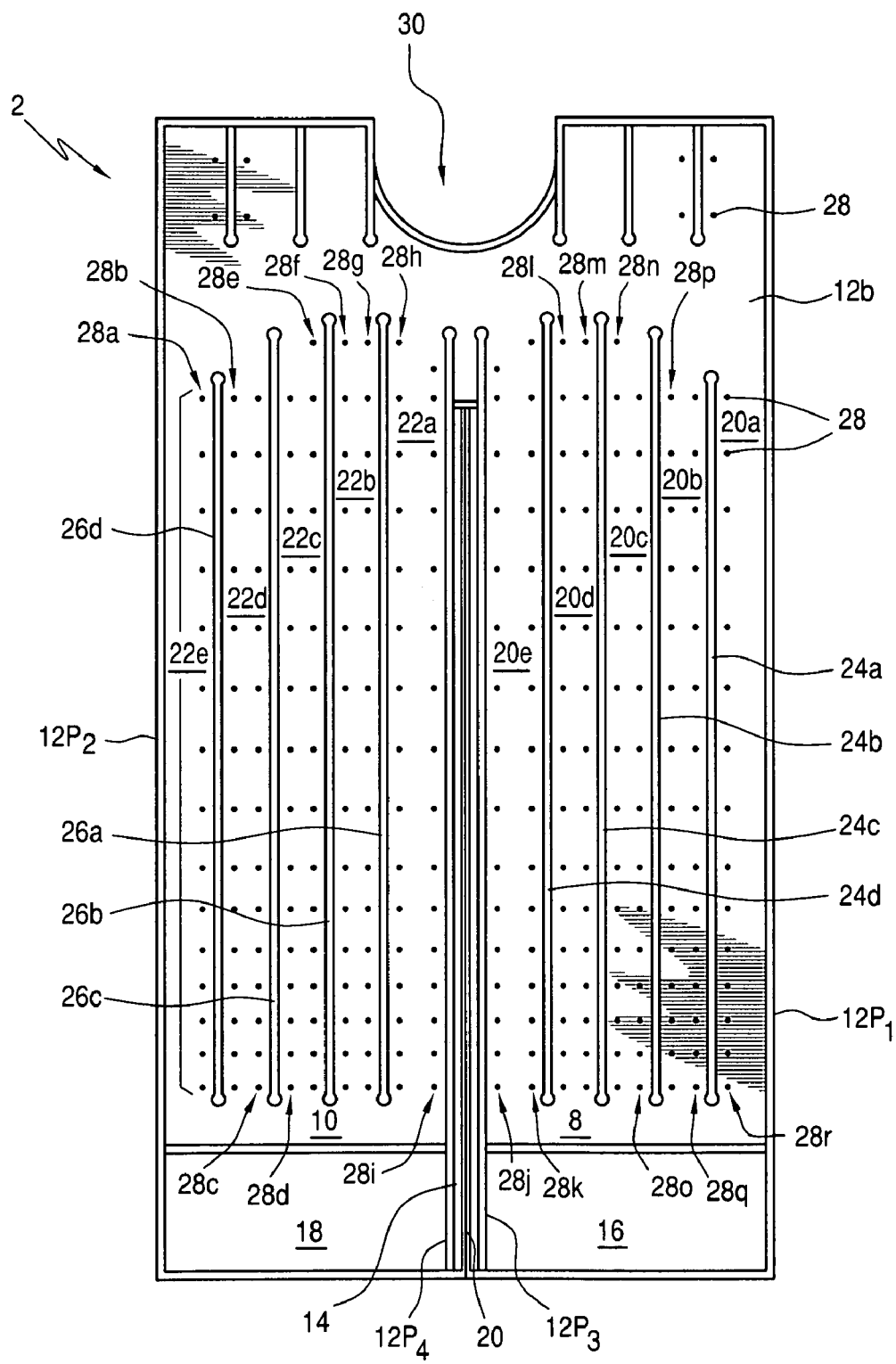
FIG. 2 is a plan view of the bottom or lower layer of the full body split access convective blanket of the present invention.

The heated air input to the blanket, for example through inlet port 28, flows through upper portion 4 and from there is directed by the various channels 20a-20e and 22a-22e to a distal area 6a for longitudinal portions 8 and 10. A plurality of apertures 28 that are provided at sheet 12b would direct the heated air onto the patient covered by blanket 2, per shown in FIG. 2. For each of the through channels 20a to 20e of longitudinal portion 8 and channel 22a-22e of longitudinal portion 10, there are provided along each of the longitudinal seals that form the channel, except for peripheral seals $12p_1$ and $12p_2$, respective longitudinal rows of apertures. By way of illustration per the exemplar bottom layer sheet shown in FIG. 2, a first row of apertures 28a is provided adjacent to one side of seal 24a while a second row of apertures 28b is provided adjacent to the other side of seal 24a for longitudinal portion 10. Similarly, respective rows of apertures 28c and 28d are provided adjacent to each side of seal 26c; respective rows of apertures 28e and 28f are formed adjacent to each side of seal 26b; and respective rows of apertures 28g and 28h are formed adjacent to each side of seal 26a. A single row of apertures 28i is provided adjacent the interior peripheral seal $12p_4$ for longitudinal portion 10. Further as shown in FIG. 2, similar rows of apertures are likewise provided adjacent the respective seals 24a-24d for longitudinal portion 8. Thus, as illustrated by the exemplar blanket of FIG. 2, there are rows of apertures 28a-28i provided longitudinally adjacent the interior seals 26d-26a and the peripheral seals $12p_2$ and $12p_4$ of longitudinal portion 10; and similar rows of apertures 28k to 28r provided longitudinally adjacent the inside peripheral seals 24d to 24a and the outside peripheral edge seals $12p_1$ and $12p_3$ of longitudinal portion 8.

There are additional apertures 28 provided in the upper portion 4 of blanket 2 for outputting heat to the shoulders, the collar bone area and the upper chest area of the patient covered by the blanket.

As further shown in FIGS. 1 and 2, there is a cut out 30 at the upper portion 4 of blanket 2. Cut out 30 ensures that the head of the patient is not covered by the blanket.

Figure 3:
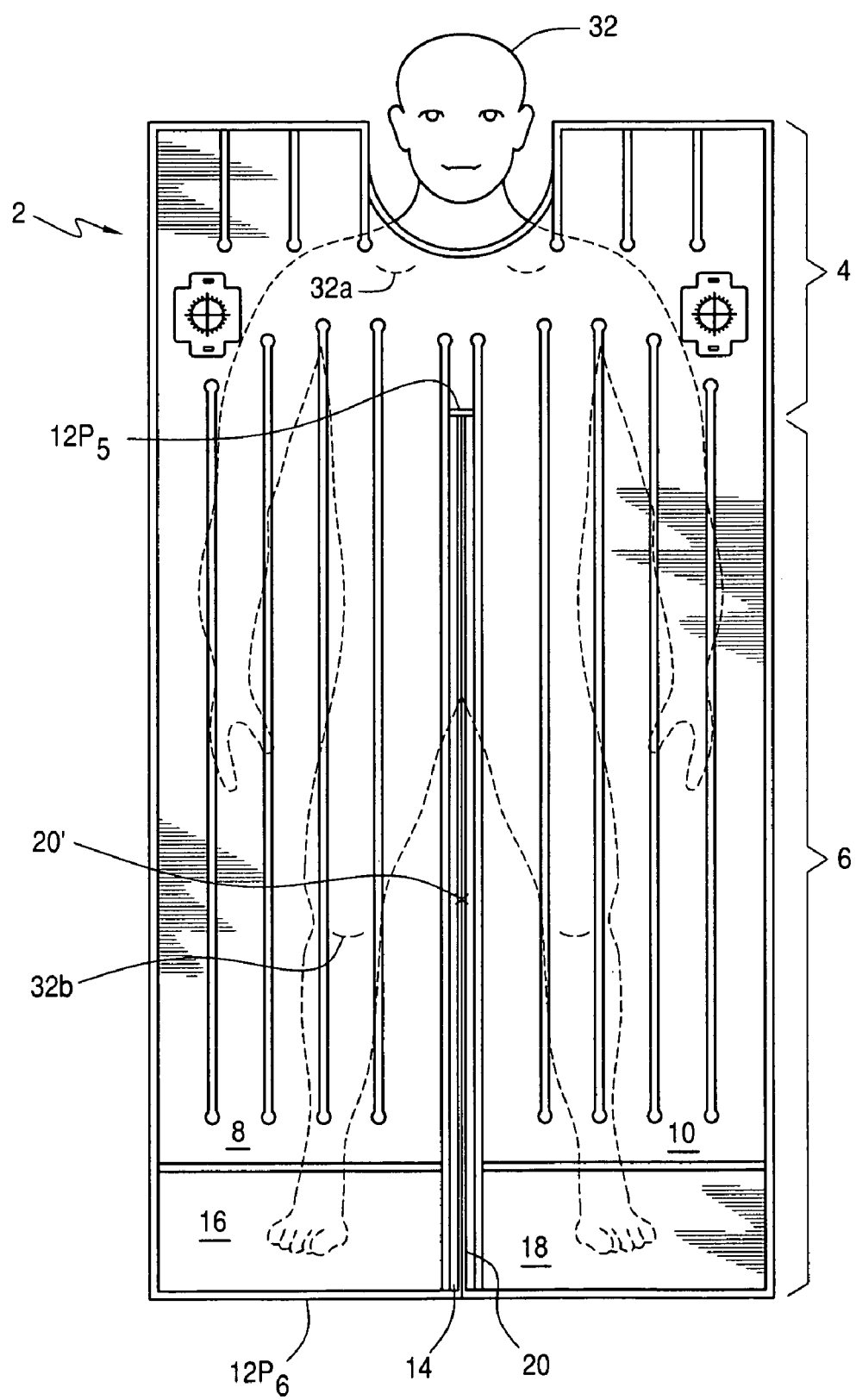
FIG. 3 is a view illustrating the full body split blanket of the present invention and its relationship to a patient covered thereby.

FIG. 3 provides an illustrative use of the present invention blanket in which a patient 32, whose body is shown mostly in phantom lines, is covered by blanket 2. As shown, upper portion 4 of blanket covers at least the shoulders and the collar bone, designated 32a, of the patient, as well as the upper chest area of the patient. Longitudinal portions 8 and 10 cover the remainder of the body of the patient starting with the lower chest area of the patient to the patient's feet. As discussed above, longitudinal portions 8 and 10 are separable from each other, so that either of those portions may be moved relative to the rest of the blanket structure. Given that the discontinuous slit or tearable line 20 extends from the foot end, designated by bottom edge seal $12p_6$, to the distal end 4a of upper portion 4, more particularly the edge seal $12p_5$, each of the longitudinal portions 8 and 10 can be selectively separated from the other longitudinal portion anywhere along the length of strip 14 to expose selective body areas of the patient. In other words, if the patient's right knee 32b were to be operated on, longitudinal portion 8 only needs to be separated from longitudinal portion 10 up to location 20' proximally above the right knee. The clinician only needs to tear along the slit 20 up to point 20', and then fold longitudinal portion 8 over, to expose the right knee 32b of the patient.

Figure 4:
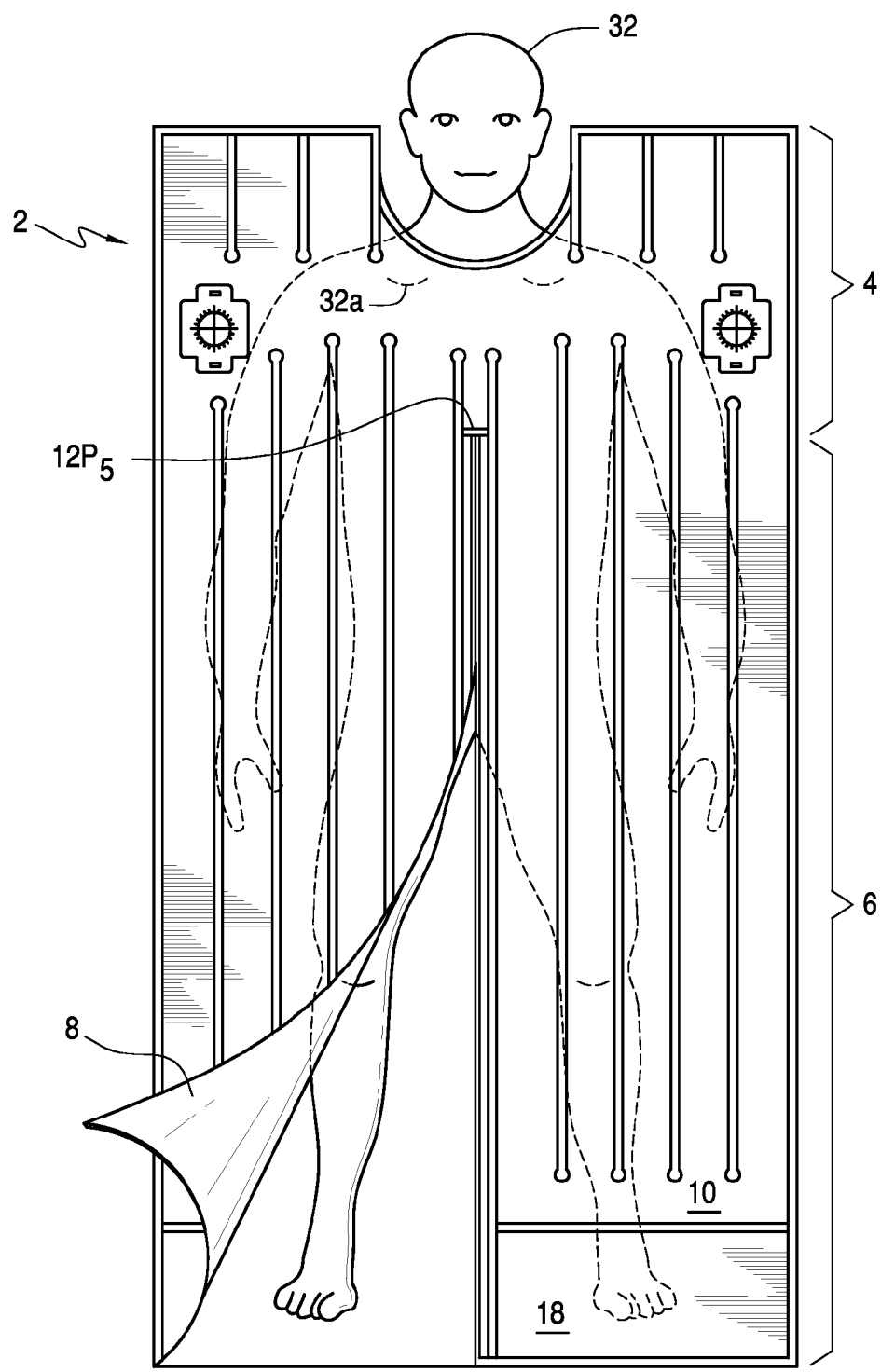
FIG. 4 is a view illustrating one of the longitudinal portions separated from the rest of the blanket to partially expose the patient.

FIG. 4 shows portion 8 having been partially separated from the rest of the blanket to expose the right leg of the patient.

Other areas of the body of the patient may similarly be selectively exposed so that the surgeon can gain access to those body areas. For example, the longitudinal portion 10 may be detached or removed from longitudinal portion 8 by tearing along slit 20 so that longitudinal portion 10 may be folded over and positioned above the stomach area of the patient to gain access to the left half of the stomach area of the patient. After the procedure to the left side of the stomach area of the patient is done, longitudinal portion 10 may be returned to its original position to cover the left side of the patient to maintain warmth thereat. Longitudinal portion 8 may then be folded back to expose the right side of the stomach area of the patient. As a result, the blanket of the present invention allows more of the body of the patient to be covered during surgery. Putting it differently, only those body areas of the patient that are to be operated on are uncovered during surgery, as the removed longitudinal portions can be returned to their original positions to re-cover the exposed body area after a procedure thereat.

Although the exemplar blanket discussed above shows two longitudinal portions 8 and 10 of equal width, it should be appreciated that instead of two longitudinal portions, there may be in fact a greater number of longitudinal portions that are separatable from each other, so that a narrower selective area of the patient may be exposed. For example, instead of two equal width longitudinal portions, there may be 3 or more equal width or non-equal width longitudinal portions extending from the upper portion of the blanket. With a greater number of longitudinal portions, a smaller area of the patient is exposed, due to the greater number of longitudinal portions and their narrower widths. These longitudinal portions are non-removably attached to each other in the same way as discussed above, in that adjacent portions are removably connected by a bonded strip with either a discontinuous slit or tearable line along the strip to enable the adjacent longitudinal portions to be detached from each other. Further, even though the upper portion 4 for the exemplar blanket of the present invention is shown to cover the upper chest area of the patient, it should be appreciated that the distal end of the upper portion 4 may in practice be moved further up or down relative to that shown in FIG. 3, so that more or less of the body of the patient may be covered/uncovered by the selective removal of the longitudinal portions of the blanket.

The invention claimed is:

1. A convective warming blanket comprising: two air impermeable sheets bonded at their respective edges to form an inflatable structure that covers the body of a patient, the structure having an upper portion that covers at least the shoulders and an area proximate to the collarbone of the patient and a body portion that includes at least two longitudinal portions each extending from said upper portion to the foot end of the blanket, said longitudinal portions removably attached to each other by a common bonded strip that extends longitudinally along the respective lengths of said longitudinal portions having a discontinuous slit or tearable line therealong so that said longitudinal portions are separable from each other along the strip, and wherein one of said longitudinal portions, when separated from other of the longitudinal portions, is movable away from the body of the patient independently from the rest of the structure to expose an area of the body of the patient covered by said one longitudinal portion.

2. Blanket of claim 1, wherein said one longitudinal portion is separable from the other longitudinal portion selectively along the length of the strip so that either of the one and other longitudinal portions is movable away from the patient at a desired length to expose a desired area of the body of the patient.

3. Blanket of claim 1, further comprising at least one inlet to enable temperature treated air to be input to said structure for inflating the same, the sheet in contact with the patient having apertures for outputting the temperature treated air to the patient.

4. Blanket of claim 1, wherein said structure is configured to have a plurality of channels wherethrough the temperature treated air passes, each of the channels being formed by adjacent spaced apart seals longitudinally extending from the upper portion to a distal area of said structure.

5. Blanket of claim 4, further comprising longitudinal rows of apertures formed on the sheet in contact with the patient, respective ones of the rows of apertures formed in alignment adjacent corresponding ones of the seals that form the channels along the longitudinal portions.

6. Blanket of claim 1, further comprising a cut out at the upper portion of the structure to enable the head of the patient to be exposed when the blanket is placed over the patient.

7. Blanket of claim 1, further comprising a sealed foot portion at a distal area at each of the longitudinal portions.

8. Blanket of claim 1, wherein the longitudinal portions have equal widths.

9. A convective warming blanket for covering the body of a patient comprising: an inflatable structure having an upper portion, at least two longitudinal portions extending from said upper portion to a foot end of the structure, the longitudinal portions removably connected by a bonded strip that extends longitudinally along the respective lengths of said longitudinal portions so as to allow said longitudinal portions to be separable at different lengths therealong so that either one or other of the two longitudinal portions is movable relative to the rest of the structure away from the patient to allow access to selective parts of the body of the patient covered by the structure, said structure having at least one inlet to enable temperature treated air to be input to the structure.

10. Blanket of claim 9, wherein said bonded strip comprises a discontinuous slit or a tearable seal centered thereon that extends from the upper portion to the foot end of said structure to allow the one and other longitudinal portions to be separable from each other selectively along any given distance of the strip so that a particular length of either of the one and other longitudinal portions may be separated from said structure to expose a particular part of the body of the patient.

11. Blanket of claim 9, further comprising at least one inlet to enable temperature treated air to be input to said structure for inflating the same.

12. Blanket of claim 9, wherein said structure comprises a plurality of channels extending at least along the one and other longitudinal portions, two longitudinal rows of apertures formed along some of the channels of said structure facing the patient when the patient is covered by said structure for outputting the temperature treated air to the patient.

13. Blanket of claim 9, further comprising a cut out at the upper portion of said structure to enable the head of the patient to be exposed when the blanket is placed over the patient.

14. Blanket of claim 9, wherein the one and other longitudinal portions each extend from the upper portion to a corresponding sealed foot portion that covers the feet of the patient.

15. A full body convective warming blanket allowing access to selective areas of the body of a patient covered thereby formed by two air impermeable sheets sealed at their respective edges, the blanket comprising:
- an upper portion;
- at least one and one other longitudinal portions removably connected to each other by a bonded strip extending longitudinally along the respective lengths of said longitudinal portions from said upper portion to a foot end of the blanket, said bonded strip being tearable such that any section of the one and other longitudinal portions is separable from each other along the length of the strip to enable the one or other of the longitudinal portions to be removed from the body of the patient so as to expose selective parts of the body of the patient;
- at least one inlet to allow heated air to be input into the blanket to inflate the blanket;
- a plurality of channels formed longitudinally along each of the one and other longitudinal portions for guiding the flow of the heated air along the blanket: and
- multiple rows of apertures formed at the sheet in contact with the patient for outputting the heated air to the patient.

16. Blanket of claim 15, wherein said bonded strip comprises a discontinuous slit or a tearable seal centered thereon that extends along the length of said strip to allow the one and other longitudinal portions to be separated from each other anywhere therealong so that a particular length of either of the one and other longitudinal portions may be separated and removed relative to the blanket to expose a particular part of the body of the patient.

17. Blanket of claim 15, wherein said plurality of channels each extend at least along the one and other longitudinal portions, two longitudinal rows of apertures formed along most of said channels at the sheet that faces the patient for outputting the temperature treated air to the patient.

18. Blanket of claim 15, further comprising a cut out at the upper portion to enable the head of the patient to be exposed when the blanket is placed over the patient.

19. Blanket of claim 15, wherein said one and other longitudinal portions each extend from said upper portion to a corresponding sealed foot portion that covers the feet of the patient.

20. Blanket of claim 15, wherein each of said multiple rows of apertures is formed in alignment adjacent a corresponding one of the seals that form the channels along the longitudinal portions.

* * * * *